(12) United States Patent
Elmalak et al.

(10) Patent No.: US 11,559,670 B2
(45) Date of Patent: Jan. 24, 2023

(54) BLADDER ROLLING MACHINE

(71) Applicant: Ortho-Space Ltd., Caesarea (IL)

(72) Inventors: Omar Elmalak, Jat (IL); Yoav Meiraz, Avihail (IL); Gad Harif, Kibbutz Metzer (IL); Gregory Rinberg, Haifa (IL)

(73) Assignee: Ortho-Space Ltd.

( * ) Notice: Subject to any disclaimer, the term of this patent is extended or adjusted under 35 U.S.C. 154(b) by 405 days.

(21) Appl. No.: 16/616,269

(22) PCT Filed: May 18, 2018

(86) PCT No.: PCT/IB2018/053533
§ 371 (c)(1),
(2) Date: Nov. 22, 2019

(87) PCT Pub. No.: WO2018/215902
PCT Pub. Date: Nov. 29, 2018

(65) Prior Publication Data
US 2020/0139091 A1 May 7, 2020

Related U.S. Application Data

(60) Provisional application No. 62/510,100, filed on May 23, 2017.

(51) Int. Cl.
*A61M 25/10* (2013.01)
*B65H 18/16* (2006.01)
(Continued)

(52) U.S. Cl.
CPC ......... *A61M 25/1038* (2013.01); *B65H 18/16* (2013.01); *A61B 17/0218* (2013.01);
(Continued)

(58) Field of Classification Search
CPC .............. A61M 25/10; A61M 25/1002; A61M 25/1027; A61M 25/1029; A61M 25/1036;
(Continued)

(56) References Cited

U.S. PATENT DOCUMENTS

| 4,415,128 A | 11/1983 | Heymanns |
| 4,681,092 A * | 7/1987 | Cho ...................... A61M 25/10 600/18 |

(Continued)

FOREIGN PATENT DOCUMENTS

| JP | H09240597 A | 9/1997 |
| JP | 2006271678 A | 10/2006 |

(Continued)

OTHER PUBLICATIONS

International Search Report from PCT/IB2018/053533, dated Sep. 26, 2018, 2 pages.

*Primary Examiner* — Kathleen S Holwerda
*Assistant Examiner* — Kankindi Rwego
(74) *Attorney, Agent, or Firm* — Lerner, David, Littenberg, Krumholz & Mentlik, LLP

(57) ABSTRACT

An apparatus for rolling a bladder includes a support structure, a rolling pin, and a bladder-mounting pin. The apparatus optionally includes a rolling initiator Rolling a bladder includes inserting the bladder while unrolled into an apparatus for rolling a bladder, inserting the bladder between a rolling pin and a bladder-mounting pin of the rolling machine, and rotating the rolling pin to (a) advance a portion of the bladder between the rolling pin and the bladder-mounting pin, (b) roll the portion of the bladder around the bladder-mounting pin, and (c) drive the bladder-mounting pin to rotate in an opposite direction from that of the rolling pin.

16 Claims, 11 Drawing Sheets

(51) Int. Cl.
*A61B 17/00* (2006.01)
*A61B 17/02* (2006.01)

(52) U.S. Cl.
CPC ............... *A61B 2017/00526* (2013.01); *A61B 2017/00557* (2013.01); *A61M 25/1002* (2013.01); *A61M 2025/1004* (2013.01)

(58) Field of Classification Search
CPC ...... A61M 25/1038; A61M 2025/1004; A61M 29/00; A61M 2029/025; B65H 18/16; B64B 1/40; B64B 1/58; A63H 27/10; A63H 2027/1025; A63H 2027/1041; A61B 17/0218; A61B 17/8855; A61B 2017/00526; A61B 2017/00557; A61B 2017/320048; A61B 2017/3486; A61B 1/00; A61B 1/00082; A61B 5/6853; A61B 2018/0025; A61B 2018/00285; A61F 2/958
USPC ................................ 242/571.1; 606/191, 192
See application file for complete search history.

(56) References Cited

U.S. PATENT DOCUMENTS

| | | | |
|---|---|---|---|
| 5,232,173 A | | 8/1993 | Planeta |
| 5,632,761 A | | 5/1997 | Smith et al. |
| 5,720,762 A | | 2/1998 | Bass |
| 5,783,227 A | * | 7/1998 | Dunham ............ A61M 25/1038 425/318 |
| 5,803,901 A | | 9/1998 | Chin et al. |
| 5,839,680 A | | 11/1998 | Biagiotti |
| 6,258,113 B1 | * | 7/2001 | Adams ................ A61B 17/0218 604/915 |
| 6,361,543 B1 | | 3/2002 | Chin et al. |
| 6,988,881 B2 | * | 1/2006 | Motsenbocker .. A61M 25/1002 29/237 |
| 7,018,392 B2 | | 3/2006 | Hudson et al. |
| 7,618,252 B1 | * | 11/2009 | Goff .................. A61M 25/1038 29/237 |
| 7,758,605 B2 | * | 7/2010 | McMorrow ....... A61M 25/1038 606/191 |
| 7,762,804 B1 | * | 7/2010 | Stupecky .......... A61M 25/1038 425/392 |
| 8,221,442 B2 | | 7/2012 | Domb et al. |
| 8,480,647 B2 | | 7/2013 | Shohat et al. |
| 8,753,390 B2 | | 6/2014 | Shohat |
| 8,894,713 B2 | | 11/2014 | Shohat et al. |
| 10,201,325 B2 | * | 2/2019 | Shohat .......... A61B 17/320016 |
| 2008/0033471 A1 | | 2/2008 | Paz et al. |
| 2010/0137999 A1 | | 6/2010 | Shohat |
| 2012/0330340 A1 | | 12/2012 | Shohat |
| 2019/0239849 A1 | | 8/2019 | Shohat |

FOREIGN PATENT DOCUMENTS

| | | |
|---|---|---|
| WO | 2008111073 A2 | 9/2008 |
| WO | 2010097724 A1 | 9/2010 |
| WO | 2012017438 A1 | 2/2012 |
| WO | 2013057566 A2 | 4/2013 |

* cited by examiner

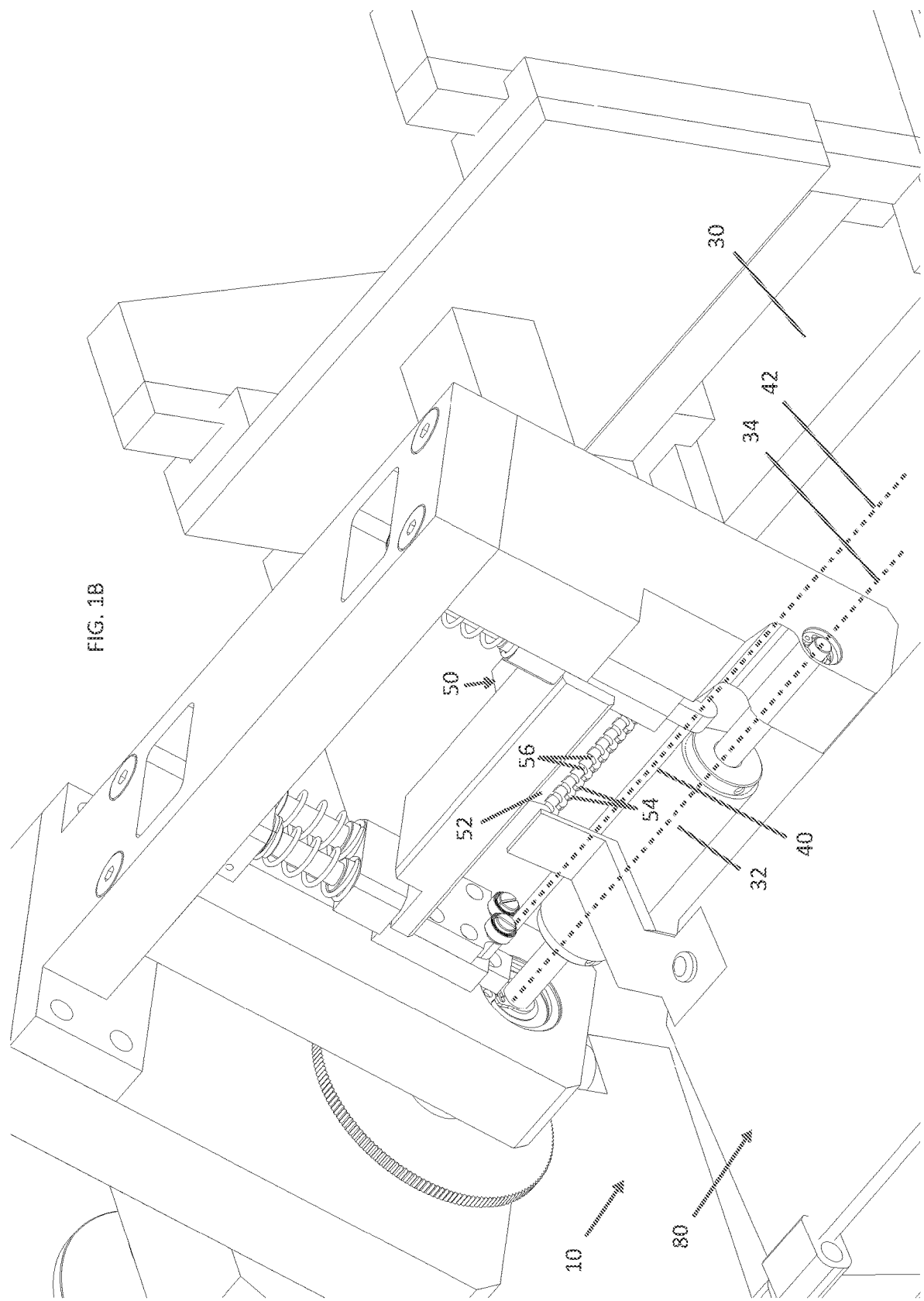

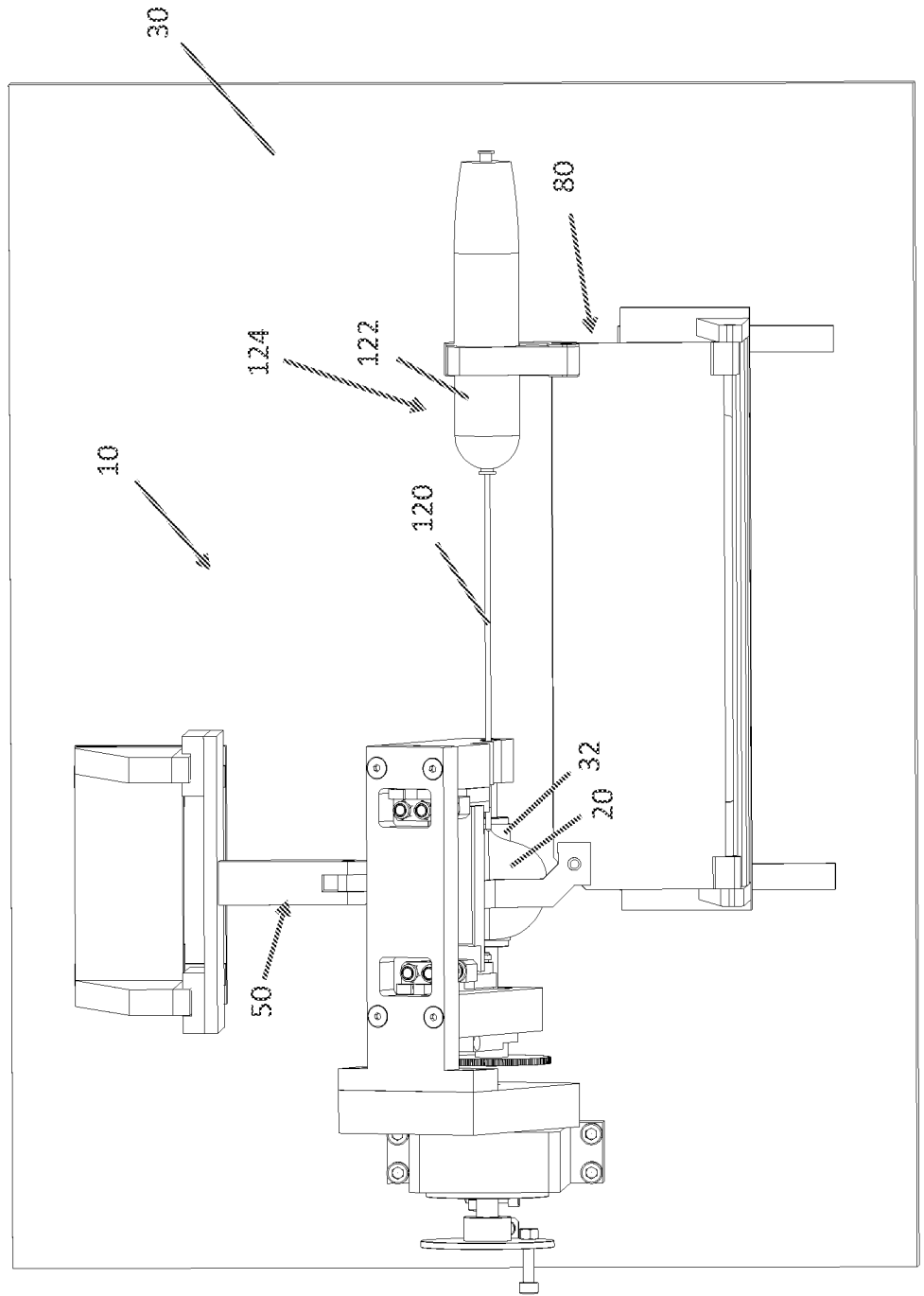

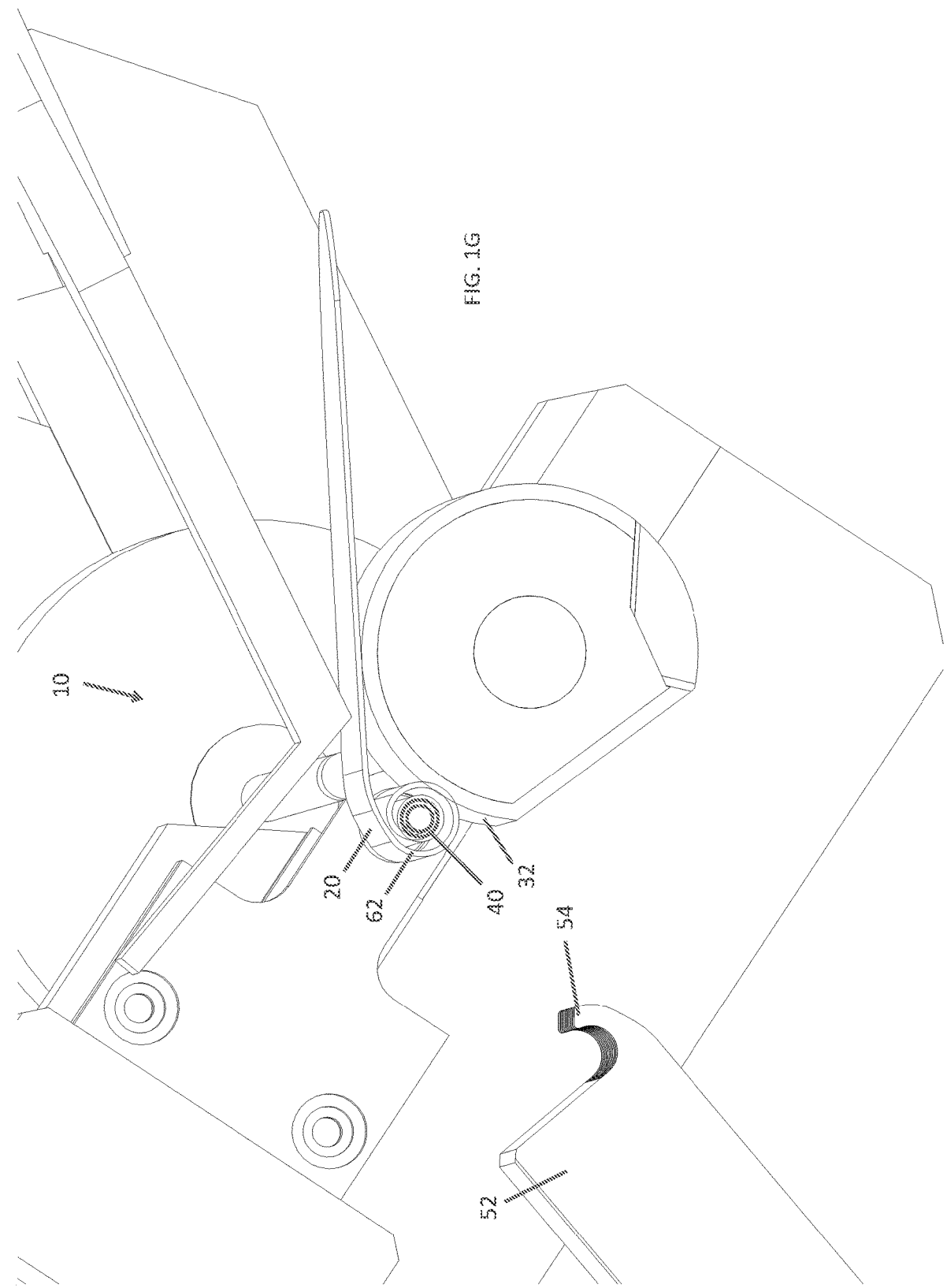

BLADDER ROLLING MACHINE

CROSS REFERENCE TO RELATED APPLICATION

The present application is a national phase entry under 35 U.S.C. § 371 of International Application No. PCT/IB2018/053533 filed May 18, 2018, published in English, which claims priority from U.S. Provisional Application No. 62/510,100 filed May 23, 2017, all of which are incorporated herein by reference.

TECHNICAL FIELD

The present invention relates generally to manufacturing equipment, and specifically to machines and methods for folding balloons.

BACKGROUND

Inflatable members, such as balloons, are sometimes rolled, such as for medical applications, such as insertion into an implantation site in a human body, e.g., a joint, such as the shoulder joint, the prostate, or the stomach, or for non-medical applications, such as for toys.

Through repeated strenuous motion, sensitive soft tissues often suffer wear and tear injuries from repeatedly rubbing against one another and/or hard tissues, such as bone. Tears of rotator cuff tendons and articular capsule disintegration are examples of this type of injury. In addition, these tissues can be adversely affected by inflammation, infection, disease and/or genetic predispositions which lead to degeneration of these tissues.

SUMMARY

A bladder rolling machine for rolling a bladder is described. The bladder rolling machine includes:
  a support structure;
  a rolling pin, which is mounted to the support structure such that the rolling pin is rotatable about a first axis, and which is optionally shaped so as to define a plurality of grooves;
  a bladder-mounting pin, which is removably mounted to the support structure such that the bladder-mounting pin is rotatable about a second axis that is non-coaxial with and parallel to the first axis; and
  optionally, a rolling initiator, which is (a) shaped so as to define a shim that defines a plurality of teeth having concavely curved surfaces, and (b) mounted to the support structure such that the shim of the rolling initiator is disposable partially between the rolling pin and the bladder-mounting pin.

For some applications in which the rolling machine includes the rolling initiator, the rolling initiator, the rolling pin, and the bladder-mounting pin are arranged such that when the rolling initiator is disposed partially between the rolling pin and the bladder-mounting pin:
  the teeth are disposed partially within the grooves of the rolling pin, respectively, and
  the concavely curved surfaces face and partially surround the second axis of the bladder-mounting pin.

As a result, the rolling initiator is configured to insert an edge of the bladder between the rolling pin and the bladder-mounting pin and partially roll the bladder around the bladder-mounting pin.

The rolling pin and the bladder-mounting pin hold the bladder in place during the rolling process. The rolling pin and the bladder-mounting pin are arranged such that rotation of the rolling pin (a) advances, by friction, a portion of the bladder (which is currently unrolled) between the rolling pin and the bladder-mounting pin, (b) rolls the portion of the bladder around the bladder-mounting pin, and (c) drives the bladder-mounting pin to rotate in an opposite direction from that of the rolling pin.

For some applications, the bladder-mounting pin is a first bladder-mounting pin, which is removably mounted to the support structure at a pin mount of the support structure, and the rolling machine includes a second bladder-mounting pin that is mountable to the rolling machine at the pin mount after the first bladder-mounting pin is dismounted from the pin mount, such that the second bladder-mounting pin is rotatable about the second axis.

For some applications, the bladder is rolled, using a two-phase rolling process, about two different axes (defined by the first and the second bladder-mounting pins before they are removed), rather than about a single central axis. Such two-axis rolling facilitates easy unrolling of the two portions (e.g., halves) of the bladder in small and narrow spaces, e.g., spaces in human joints, such as between a ball and socket. For some applications, the first portion and the second portion are rolled in the same direction around their respective central axes, such that the bladder is rolled in an overly curled S-shape. For other applications, the first portion and the second portion are rolled in opposite directions around their respective central axes, such that the bladder is rolled in a cassette-tape-like configuration.

There is therefore provided apparatus including a rolling machine for rolling a bladder, the rolling machine including:
  a support structure;
  a rolling pin, which is mounted to the support structure such that the rolling pin is rotatable about a first axis, and which is shaped so as to define a plurality of grooves;
  a bladder-mounting pin, which is removably mounted to the support structure such that the bladder-mounting pin is rotatable about a second axis that is non-coaxial with and parallel to the first axis; and
  a rolling initiator, which is (a) shaped so as to define a shim that defines a plurality of teeth having concavely curved surfaces, and (b) mounted to the support structure such that the shim of the rolling initiator is disposable partially between the rolling pin and the bladder-mounting pin,
  wherein the rolling initiator, the rolling pin, and the bladder-mounting pin are arranged such that when the rolling initiator is disposed partially between the rolling pin and the bladder-mounting pin, the teeth are disposed partially within the grooves of the rolling pin, respectively, and the concavely curved surfaces face and partially surround the second axis of the bladder-mounting pin, such that the rolling initiator is configured to insert an edge of the bladder between the rolling pin and the bladder-mounting pin and partially roll the bladder around the bladder-mounting pin, and
  wherein the rolling pin and the bladder-mounting pin are arranged such that rotation of the rolling pin (a) advances, by friction, a portion of the bladder between the rolling pin and the bladder-mounting pin, (b) rolls the portion of the bladder around the bladder-mounting pin, and (c) drives the bladder-mounting pin to rotate in an opposite direction from that of the rolling pin.

For some applications, a radius of curvature of the concavely curved surfaces of the teeth equals between 50% and 150% of a radius of the bladder-mounting pin.

For some applications, the rolling initiator, the rolling pin, and the bladder-mounting pin are arranged such that when the rolling initiator is disposed partially between the rolling pin and the bladder-mounting pin, respective portions of the concavely curved surfaces are flush with or recessed with respect to an outer surface of the rolling pin axially between the grooves.

For some applications, the rolling machine further includes a feeding unit, which is configured to removably hold the bladder during rolling of the bladder around the bladder-mounting pin.

For some applications, a radius of the bladder-mounting pin is no more than 50% of a radius of the rolling pin. Alternatively or additionally, for some applications, a radius of the bladder-mounting pin is between 0.8 and 4 mm.

For some applications, a radius of the rolling pin is between 8 and 25 mm.

For some applications, the rolling machine further includes one or more gears that are arranged to rotate the rolling pin.

For some applications, the apparatus further includes a clamp, which is configured to hold the bladder in a partially rolled state around the bladder-mounting pin.

For some applications:

the bladder-mounting pin is a first bladder-mounting pin, which is removably mounted to the support structure at a pin mount of the support structure, and the rolling machine includes a second bladder-mounting pin that is mountable to the rolling machine at the pin mount after the first bladder-mounting pin is dismounted from the pin mount, such that the second bladder-mounting pin is rotatable about the second axis.

For some applications, the rolling machine is configured to maintain a predetermined air temperature range in a vicinity of the rolling pin. For some applications, the predetermined air temperature range has a low end of between 40 and 53 degrees C. and a high end of between 50 and 65 degrees C. For some applications, the predetermined air temperature range has a low end of between 50 and 51.5 degrees C. and a high end of between 50.5 and 53 degrees C.

There is further provided a method for rolling a bladder, the method including:

inserting the bladder while unrolled into a rolling machine;

using a rolling initiator, which is mounted to a support structure of the rolling machine, to insert an edge of the bladder between a rolling pin and a bladder-mounting pin of the rolling machine, wherein the rolling pin is mounted to the support structure such that the rolling pin is rotatable about a first axis, and the bladder-mounting pin is removably mounted to the support structure such that the bladder-mounting pin is rotatable about a second axis that is non-coaxial with and parallel to the first axis; and rotating the rolling pin to (a) advance, by friction, a portion of the bladder between the rolling pin and the bladder-mounting pin, (b) roll the portion of the bladder around the bladder-mounting pin, and (c) drive the bladder-mounting pin to rotate in an opposite direction from that of the rolling pin.

For some applications, the bladder includes a medical device.

For some applications:

the rolling initiator is mounted to the support structure such that the rolling initiator is disposable partially between the rolling pin and the bladder-mounting pin, the rolling pin is shaped so as to define a plurality of grooves, the rolling initiator is shaped so as to define a shim that defines a plurality of teeth having concavely curved surfaces, the rolling initiator, the rolling pin, and the bladder-mounting pin are arranged such that when the rolling initiator is disposed partially between the rolling pin and the bladder-mounting pin, the teeth are disposed partially within the grooves of the rolling pin, respectively, and the concavely curved surfaces face and partially surround the second axis of the bladder-mounting pin, and rotating the rolling pin includes rotating the rolling pin such that the rolling initiator partially rolls the bladder around the bladder-mounting pin when inserting the edge of the bladder between the rolling pin and the bladder-mounting pin.

For some applications, a radius of curvature of the concavely curved surfaces of the teeth equals between 50% and 150% of a radius of the bladder-mounting pin.

For some applications, the rolling initiator, the rolling pin, and the bladder-mounting pin are arranged such that when the rolling initiator is disposed partially between the rolling pin and the bladder-mounting pin, respective portions of the concavely curved surfaces are flush with or recessed with respect to an outer surface of the rolling pin axially between the grooves.

For some applications, inserting the bladder into the rolling machine includes removably coupling the bladder to a feeding unit of the rolling machine, which is configured to removably hold the bladder during rolling of the bladder around the bladder-mounting pin.

For some applications, a radius of the bladder-mounting pin is no more than 50% of a radius of the rolling pin. Alternatively or additionally, for some applications, a radius of the bladder-mounting pin is between 0.8 and 4 mm.

For some applications, a radius of the rolling pin is between 8 and 25 mm.

For some applications, rotating the rolling pin includes using one or more gears of the rolling machine to rotate the rolling pin.

For some applications, the method further includes, after rotating the rolling pin, using a clamp to hold the bladder in a partially rolled state around the bladder-mounting pin.

For some applications, the method further includes:

removing the bladder-mounting pin from the rolled portion of the bladder; and inserting the bladder into a delivery sheath.

For some applications, rotating the rolling pin includes rotating the rolling pin while maintaining a predetermined air temperature range in a vicinity of the rolling pin. For some applications, the predetermined air temperature range has a low end of between 40 and 53 degrees C. and a high end of between 50 and 65 degrees C. For some applications, the predetermined air temperature range has a low end of between 50 and 51.5 degrees C. and a high end of between 50.5 and 53 degrees C.

For some applications:

the bladder-mounting pin is a first bladder-mounting pin, the edge of the bladder is a first edge of the bladder, and the portion of the bladder is a first portion of the bladder, using the rolling initiator includes using the rolling initiator to insert the first edge of the bladder between the first rolling pin and the first bladder-mounting pin, rotating the rolling pin includes rotating the rolling pin to (a) advance, by friction, the first portion of the bladder between the rolling pin and the first bladder-mounting pin, and (b) roll the first portion of the bladder around the first bladder-mounting pin, and the method further includes, after rotating the rolling pin to roll the first portion of the bladder around the first bladder-mounting pin:

dismounting the first bladder-mounting pin from the rolling machine;

mounting a second bladder-mounting pin to the rolling machine such that the second bladder-mounting pin is rotatable about the second axis;

using the rolling initiator to insert a second edge of the bladder between the rolling pin and the second bladder-mounting pin; and rotating the rolling pin to (a) advance, by friction, a second portion of the bladder between the rolling pin and the second bladder-mounting pin, and (b) roll the second portion of the bladder around the second bladder-mounting pin.

For some applications, the first portion of the bladder includes between 20% and 50% of a total surface area of the unrolled bladder, and the second portion of the bladder includes between 20% and 50% of a total surface area of the unrolled bladder.

For some applications, the bladder is removably coupled to an inflation rod, and the first and the second portions are on opposite sides of a central longitudinal axis of the inflation rod.

For some applications, the method further includes, after the first portion of the bladder is rolled around the first bladder-mounting pin, and before the second edge of the bladder is inserted between the rolling pin and the second bladder-mounting pin, using a clamp to hold the first rolled part rolled in place about the first bladder-mounting pin.

For some applications, the method further includes:

removing the first and the second bladder-mounting pins from the first and the second rolled portions of the bladder; and inserting the bladder into a delivery sheath.

For some applications, rotating the rolling pin to roll the first and the second portions includes rolling the first and the second portions such that the first and the second portions are rolled in a same direction around respective central axes of the first and the second portions.

For some applications, rotating the rolling pin to roll the first and the second portions includes rolling the first and the second portions such that the first and the second portions are rolled in opposite directions around respective central axes of the first and the second portions.

For some applications:

the edge of the bladder is a first edge of the bladder, and the portion of the bladder is a first portion of the bladder, using the rolling initiator includes using the rolling initiator to insert the first edge of the bladder between the first rolling pin and the bladder-mounting pin, rotating the rolling pin includes rotating the rolling pin to (a) advance, by friction, the first portion of the bladder between the rolling pin and the bladder-mounting pin, and (b) roll the first portion of the bladder around the bladder-mounting pin, and the method further includes, after rotating the rolling pin to roll the first portion of the bladder around the bladder-mounting pin:

removing the bladder-mounting pin from the first rolled portion of the bladder;

using the rolling initiator to insert a second edge of the bladder between the rolling pin and the bladder-mounting pin; and rotating the rolling pin to (a) advance, by friction, a second portion of the bladder between the rolling pin and the bladder-mounting pin, and (b) roll the second portion of the bladder around the bladder-mounting pin.

For some applications, the first portion of the bladder includes between 20% and 50% of a total surface area of the unrolled bladder, and the second portion of the bladder includes between 20% and 50% of a total surface area of the unrolled bladder.

For some applications, removing the bladder-mounting pin from the first rolled portion of the bladder includes:

dismounting the bladder-mounting pin from the rolling machine;

thereafter, removing the bladder-mounting pin from the first rolled portion of the bladder; and thereafter, mounting the bladder-mounting pin to the rolling machine such that the bladder-mounting pin is rotatable about the second axis.

For some applications, the bladder is removably coupled to an inflation rod, and the first and the second portions are on opposite sides of a central longitudinal axis of the inflation rod.

For some applications, the method further includes:

removing the bladder-mounting pin from the second rolled portion of the bladder; and inserting the bladder into a delivery sheath.

For some applications, rotating the rolling pin to roll the first and the second portions includes rolling the first and the second portions such that the first and the second portions are rolled in a same direction around respective central axes of the first and the second portions.

For some applications, rotating the rolling pin to roll the first and the second portions includes rolling the first and the second portions such that the first and the second portions are rolled in opposite directions around respective central axes of the first and the second portions.

There is further provided a method for rolling a bladder, the method including:

inserting the bladder while unrolled into a rolling machine;

inserting a first edge of the bladder between a rolling pin and a first bladder-mounting pin of the rolling machine, wherein the rolling pin is mounted to a support structure of the rolling machine such that the rolling pin is rotatable about a first axis, and the first bladder-mounting pin is removably mounted to the support structure such that the first bladder-mounting pin is rotatable about a second axis that is non-coaxial with and parallel to the first axis;

rotating the rolling pin to (a) advance, by friction, a first portion of the bladder between the rolling pin and the first bladder-mounting pin, (b) roll the first portion of the bladder around the first bladder-mounting pin, and (c) drive the first bladder-mounting pin to rotate in an opposite direction from that of the rolling pin;

dismounting the first bladder-mounting pin from the rolling machine;

mounting a second bladder-mounting pin to the rolling machine such that the second bladder-mounting pin is rotatable about the second axis;

inserting a second edge of the bladder between the rolling pin and the second bladder-mounting pin; and rotating the rolling pin to (a) advance, by friction, a second portion of the bladder between the rolling pin and the second bladder-mounting pin, and (b) roll the second portion of the bladder around the second bladder-mounting pin.

For some applications, the first portion includes between 20% and 50% of a total surface area of the unrolled bladder, and the second portion includes between 20% and 50% of the total surface area of the unrolled bladder.

For some applications, the bladder is removably coupled to an inflation rod, and the first and the second portions are on opposite sides of a central longitudinal axis of the inflation rod.

For some applications, the method further includes, after the first portion of the bladder is rolled around the first bladder-mounting pin, and before the second edge of the bladder is inserted between the rolling pin and the second bladder-mounting pin, using a clamp to hold the first rolled part rolled in place about the first bladder-mounting pin.

For some applications, the method further includes:

removing the first and the second bladder-mounting pins from the first and the second rolled portions of the bladder; and inserting the bladder into a delivery sheath.

For some applications, rotating the rolling pin to roll the first and the second portions includes rolling the first and the second portions such that the first and the second portions are rolled in a same direction around respective central axes of the first and the second portions.

For some applications, rotating the rolling pin to roll the first and the second portions includes rolling the first and the second portions such that the first and the second portions are rolled in opposite directions around respective central axes of the first and the second portions.

Implementations will be more fully understood from the following detailed description, taken together with the drawings, in which:

BRIEF DESCRIPTION OF THE DRAWINGS

FIG. 1B is a partial view of the bladder rolling machine of FIG. 1A;

FIG. 1D is a front view of the bladder rolling machine of FIG. 1A with the bladder;

FIG. 1G is a cross-sectional view of the bladder rolling machine of FIG. 1A with the bladder;

DETAILED DESCRIPTION

Figure 1A:
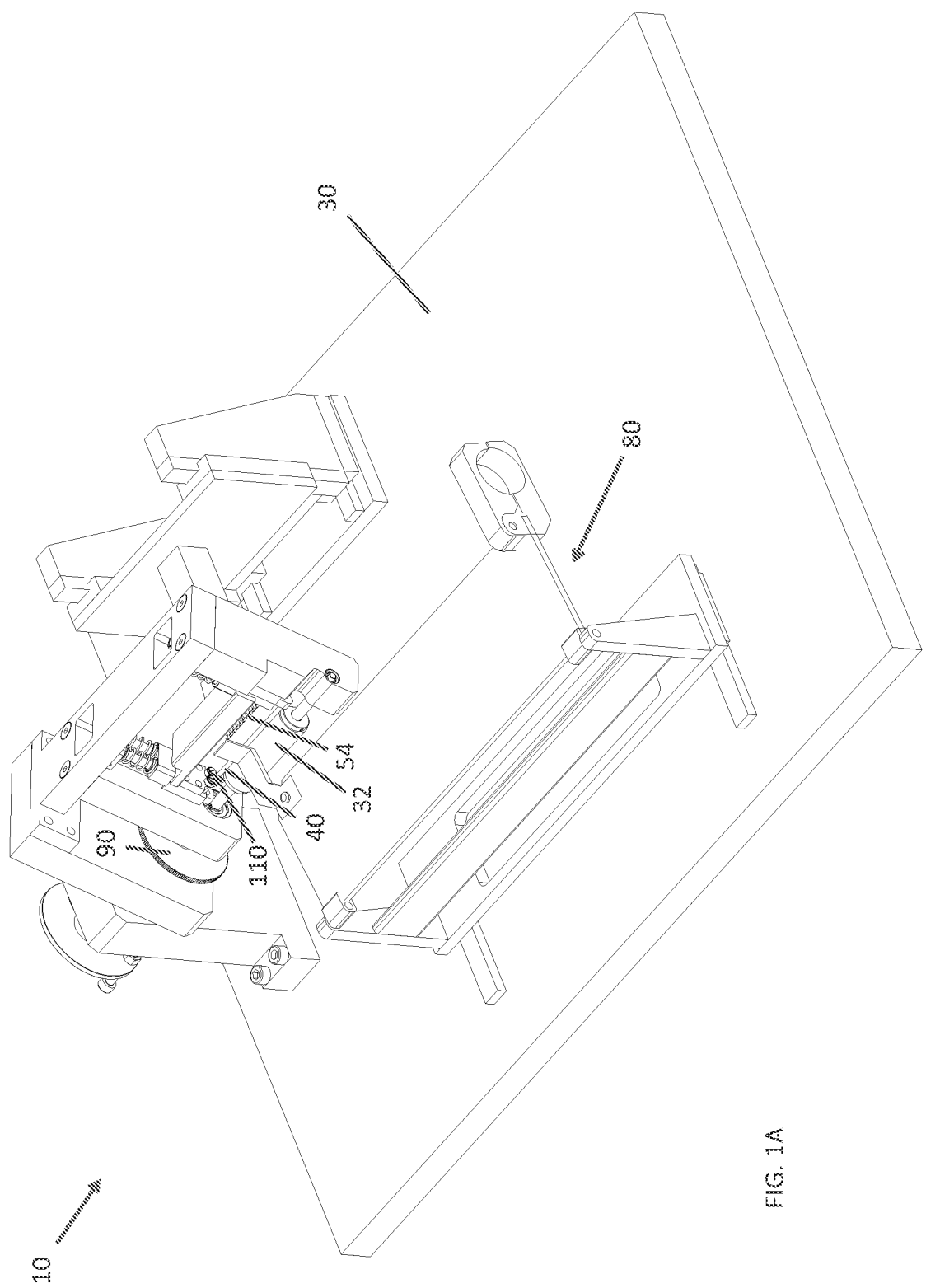
FIG. 1A is a perspective view of a bladder rolling machine for rolling a bladder.
Figure 1C:
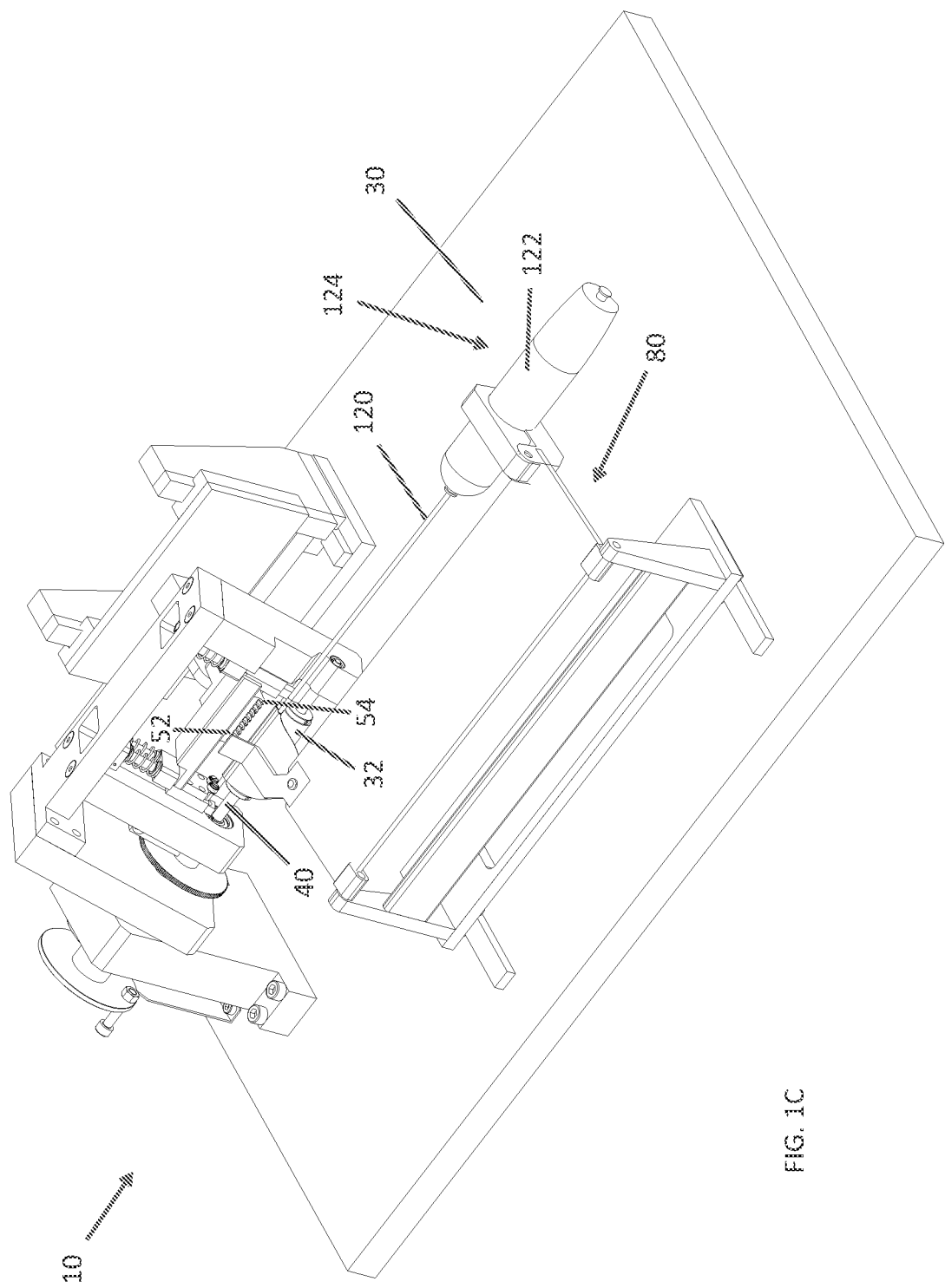
FIG. 1C is a front perspective view of the bladder rolling machine of FIG. 1A with a bladder.
Figure 1E:
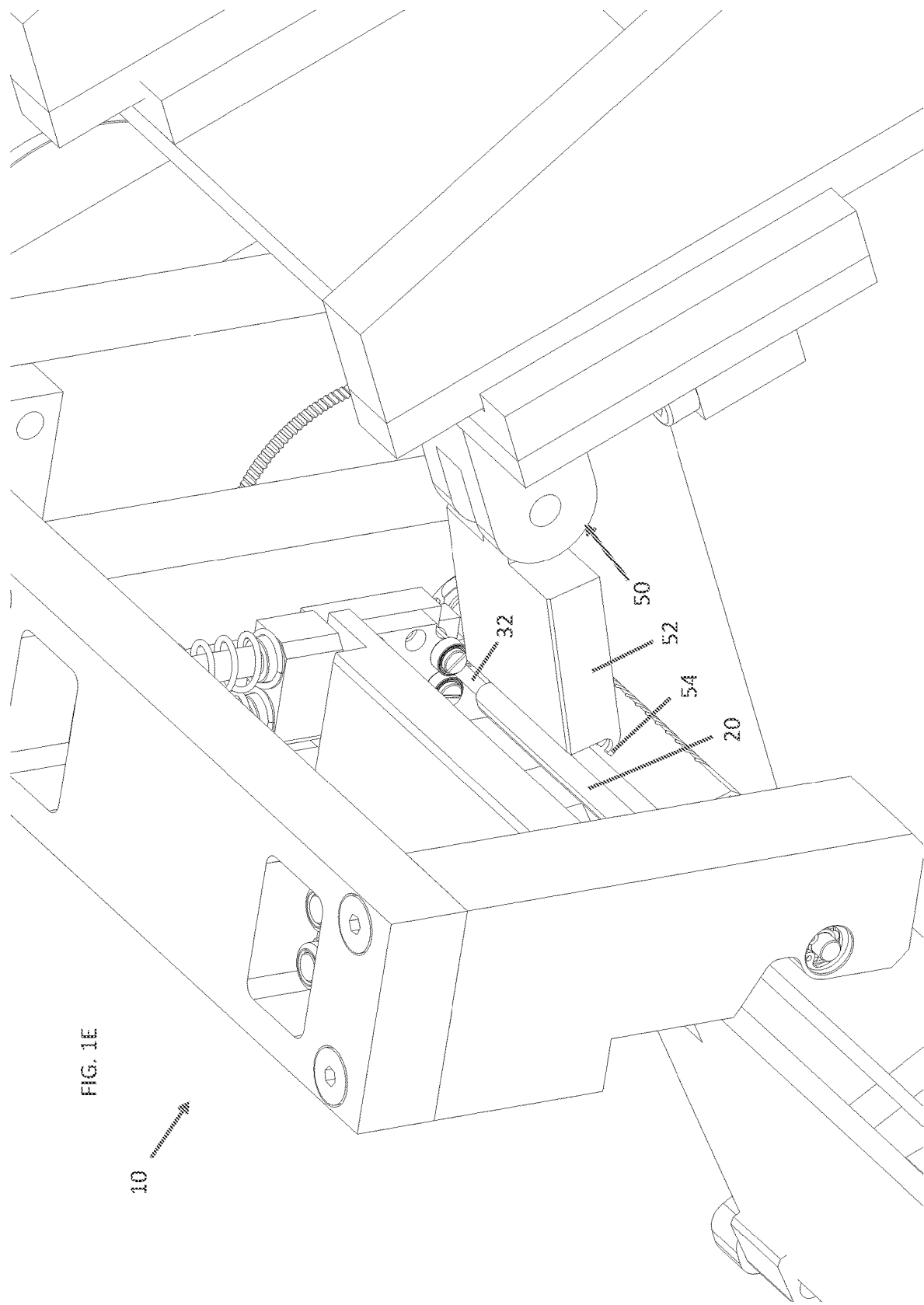
FIG. 1E is a partial view of the bladder rolling machine of FIG. 1A.
Figure 1F:
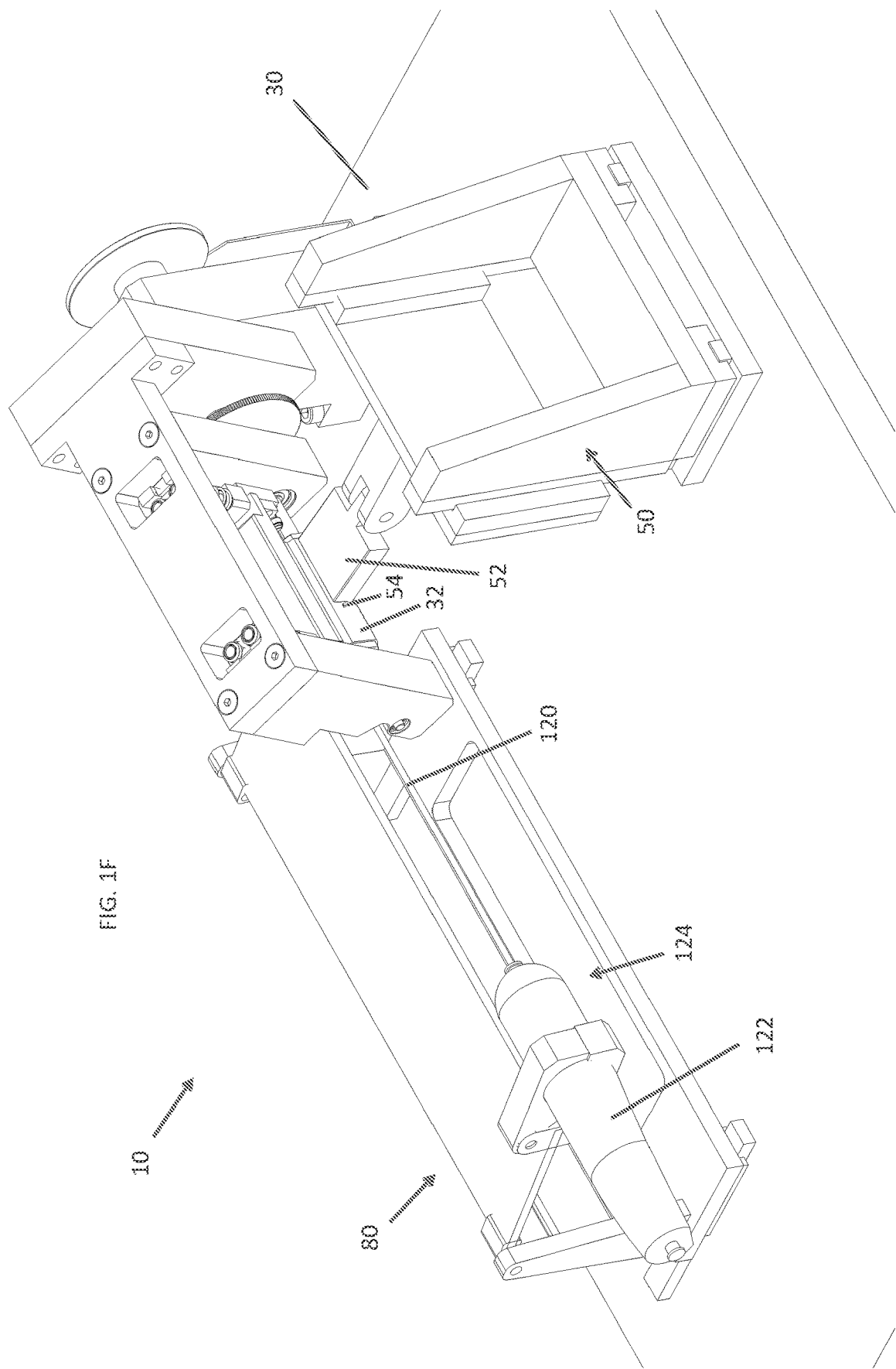
FIG. 1F is a back perspective view of the bladder rolling machine of FIG. 1A with the bladder.

FIGS. 1A-G are schematic illustrations of a bladder rolling machine 10 for rolling a bladder 20. FIGS. 1A-B show bladder rolling machine 10 without bladder 20, and FIGS. 1C-G show rolling machine 10 with bladder 20. FIG. 1G is a cross-sectional view. For some applications, bladder 20 includes an inflatable balloon, which may be elastic or generally non-compliant at the pressures ordinarily used. For some applications, bladder 20 includes a medical device, such as a joint spacer for treatment of a joint of a human subject, such as a subacromial spacer, a glenohumeral spacer, or a spacer for another joint, such as a knee, hip, ankle, or hand (e.g., CMC1) joint. The joint spacer may implement techniques described in the patents and patent application publications incorporated by reference hereinbelow. For some applications, bladder 20 includes a polymer, which, for example, may be crystalline or semi-crystalline, or a flexible metal.

Figure 2:
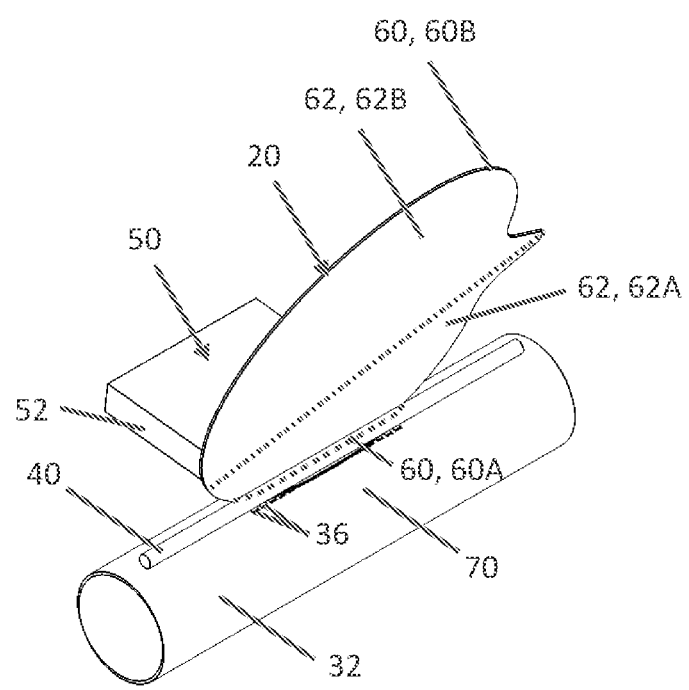
FIG. 2 is a schematic illustration of several components of the bladder rolling machine of FIG. 1.

Reference is still made to FIGS. 1A-G, and is additionally made to FIG. 2, which is a schematic illustration of several components of bladder rolling machine 10. Bladder rolling machine 10 includes:

a support structure 30;

a rolling pin 32, which is mounted to support structure 30 such that rolling pin 32 is rotatable about a first axis 34 (labeled in FIG. 1B), and which is optionally shaped so as to define a plurality of grooves 36 (labeled in FIG. 2);

a bladder-mounting pin 40, which is removably mounted to support structure 30 such that bladder-mounting pin 40 is rotatable about a second axis 42 (labeled in FIG. 1B) that is non-coaxial with and parallel to first axis 34; and optionally, a rolling initiator 50, which (a) is shaped so as to define a shim 52 that defines a plurality of teeth 54 having concavely curved surfaces 56 (labeled in FIG. 1B), and (b) optionally is mounted to support structure 30 such that shim 52 of rolling initiator 50 is disposable partially between rolling pin 32 and bladder-mounting pin 40 (as shown in FIG. 2); for some applications, a radius of curvature of concavely curved surfaces 56 of teeth 54 equals between 50% and 150% (e.g., between 80% and 120) of a radius of bladder-mounting pin 40.

For applications in which rolling machine 10 includes rolling initiator 50, rolling initiator 50 is partially inserted between rolling pin 32 and bladder-mounting pin 40, either manually by manually by the operator of bladder rolling machine 10, or automatically by bladder rolling machine 10. For some applications in which rolling machine 10 includes rolling initiator 50, rolling initiator 50, rolling pin 32, and bladder-mounting pin 40 are arranged such that when rolling initiator 50 is disposed partially between rolling pin 32 and bladder-mounting pin 40:

teeth 54 are disposed partially within grooves 36 of rolling pin 32, respectively, and concavely curved surfaces 56 face and partially surround second axis 42 of bladder-mounting pin 40.

As a result, rolling initiator 50 is configured to insert an edge 60 of bladder 20 (labeled in FIG. 2) between rolling pin 32 and bladder-mounting pin 40 and partially roll bladder 20 around bladder-mounting pin 40, such as around at least 90 degrees, e.g., at least 180 degrees, such as at least 270 of bladder-mounting pin 40, e.g., at least 360 degrees, typically no more than 375 degrees. After bladder 20 has been partially rolled around bladder-mounting pin 40, rolling initiator 50 is moved away from rolling pin 32 and bladder-mounting pin 40, either manually by the operator of bladder rolling machine 10, or automatically by bladder rolling machine 10. Typically, rolling initiator 50 is used for only one or two seconds during the rolling process.

Alternatively, bladder rolling machine 10 does not necessarily include rolling initiator 50, and rolling pin 32 is soft, flexible, and thick, so as to serve as a pillow that has sufficient curvature to enable the first round of rolling.

Rolling pin 32 and bladder-mounting pin 40 hold bladder 20 in place during the rolling process. Rolling pin 32 and bladder-mounting pin 40 are arranged such that rotation of rolling pin 32 (*a*) advances, by friction, a portion 62 of bladder 20 (which is currently unrolled) between rolling pin 32 and bladder-mounting pin 40, (*b*) rolls portion 62 of bladder 20 (labeled in FIG. 1G) around bladder-mounting pin 40, and (*c*) drives bladder-mounting pin 40 to rotate in an opposite direction from that of rolling pin 32. Typically, rolling pin 32 has a high coefficient of friction, and may include, for example, smooth or rough stainless steel, which is optionally coated with a polymer, e.g., in a vulcanization process. Typically, rolling machine 10 further includes one or more gears 90 that are arranged to rotate rolling pin 32. Bladder-mounting pin 40 is configured to maintain a desired rolling diameter.

For some applications, rolling initiator 50, rolling pin 32, and bladder-mounting pin 40 are arranged such that when rolling initiator 50 is disposed partially between rolling pin 32 and bladder-mounting pin 40, respective portions of concavely curved surfaces 56 are flush with or recessed with respect to an outer surface 70 of rolling pin 32 axially between grooves 36 (labeled in FIG. 2).

For some applications, rolling machine 10 further includes a feeding unit 80, which is configured to removably hold bladder 20 during rolling of bladder 20 around bladder-mounting pin 40. Typically, feeding unit 80 maintains tension of bladder 20 during the rolling process to allow tight and stable rolling.

For some applications, a radius of bladder-mounting pin 40 is no more than 50%, such as no more than 40%, of a radius of rolling pin 32, and/or at least 3% (e.g., at least 4%) of the radius of rolling pin 32. For some applications, the radius of bladder-mounting pin 40 is at least 0.8 mm, no more than 4 mm, and/or between 0.8 and 4 mm, such as 1.3 mm. Alternatively or additionally, for some applications, the radius of rolling pin 32 is at least 8 mm, no more than 25 mm, and/or between 8 and 25 mm.

For some applications, bladder-mounting pin 40 is a first bladder-mounting pin 40, which is removably mounted to support structure 30 at a pin mount 110 of support structure 30 (labeled in FIG. 1A), and rolling machine 10 includes a second bladder-mounting pin 40 that is mountable to rolling machine 10 at pin mount 110 after first bladder-mounting pin 40 is dismounted from pin mount 110, such that second bladder-mounting pin 40 is rotatable about second axis 42.

For some applications, rolling machine 10 is configured to maintain a predetermined air temperature range in a vicinity of rolling pin 32. For some applications, the predetermined air temperature range has a low end of between 40 and 53 degrees C. and a high end of between 50 and 65 degrees C., such as a low end of between 50 and 51.5 degrees C. and a high end of between 50.5 and 53 degrees C., e.g., the range is 51 to 53 degrees C. For some applications, the predetermined temperature range is above the glass transition of a polymer of bladder 20. Typically, the predetermined air temperature range is adjustable by an operator of rolling machine 10.

Typically, rolling machine 10 is suitable for use in a clean room. Typically, rolling machine 10 is capable of rolling bladders 20 of different sizes, and thus, for example, pin mount 110 is typically able to accommodate different rolling pin diameters.

A method of rolling bladder 20 using bladder rolling machine 10 is provided.

Bladder 20 is inserted while unrolled into rolling machine 10. For some applications, bladder 20 is inserted into rolling machine 10 by removably coupling bladder 20 to feeding unit 80.

Rolling initiator 50 is used to insert edge 60 of bladder 20 between rolling pin 32 and bladder-mounting pin 40. Before insertion between the pins, edge 60 may be flat (unrolled), or slightly rolled to aid with this initial rolling of the edge around bladder-mounting pin 40. The arrangement of grooves 36 and teeth 54, described hereinabove with reference to FIGS. 1AG and 2 may aid with this insertion.

Rolling pin 32 is rotated to (a) advance, by friction, portion 62 of bladder 20 (which is currently unrolled) between rolling pin 32 and bladder-mounting pin 40, (b) roll portion 62 of bladder 20 around bladder-mounting pin 40, and (c) drive bladder-mounting pin 40 to rotate in an opposite direction from that of rolling pin 32. It is noted that grooves 36 are too small to interfere with the rolling of bladder 20.

For some applications, the rolling is performed in two phases, in each of which a portion (typically about half) of bladder 20 is rolled around respective bladder-mounting pins 40. For these applications, bladder-mounting pin 40 is a first bladder-mounting pin 40, edge 60 of bladder 20 is a first edge 60A of bladder 20 (labeled in FIG. 2), and portion 62 of bladder 20 is a first portion 62A of bladder 20 (labeled in FIG. 2), which typically includes between 20% and 60% (e.g., between 20% and 50% (such as between 35% and 45%), or between 45% and 55%) of a total surface area of the unrolled bladder.

For some applications, a first clamp is provided and used to hold bladder 20 in a partially rolled state around first bladder-mounting pin 40.

After rolling pin 32 is rotated to roll first portion 62A of bladder 20 around the first bladder-mounting pin, first bladder-mounting pin 40 is dismounted from pin mount 110 of rolling machine 10. A second bladder-mounting pin 40 is mounted to pin mount 110 of rolling machine 10 such that second bladder-mounting pin 40 is rotatable about second axis 42. Rolling initiator 50 is used to insert a second edge 60B of bladder 20 (labeled in FIG. 2) between rolling pin 32 and second bladder-mounting pin 40. Before insertion between the pins, second edge 60B may be flat (unrolled), or slightly rolled to aid with this initial rolling of the second edge around second bladder-mounting pin 40. The arrangement of grooves 36 and teeth 54, described hereinabove with reference to FIGS. 1A-G and 2 may aid with this insertion.

Rolling pin 32 is rotated to (a) advance, by friction, second portion 62B of bladder 20 between rolling pin 32 and second bladder-mounting pin 40, and (b) roll second portion 62B of bladder 20 around second bladder-mounting pin 40. Typically, second portion 62B of bladder 20 includes between 20% and 60% (e.g., between 20% and 50% (such as between 35% and 45%), or between 45% and 55%) of the total surface area of the unrolled bladder. Alternatively or additionally, bladder 20 is removably coupled to a delivery rod 120 (labeled in FIGS. 1C, 1D, and 1F), and first and second portions 62A and 62B are on opposite sides of a central longitudinal axis of delivery rod 120. For some applications, delivery rod 120 is used to inflate the bladder after implantation of the bladder in the human body. (FIGS. 1C, 1D, and 1F also show a handle 122 of a delivery system 124 used for implanting bladder 20.)

Figure 4:
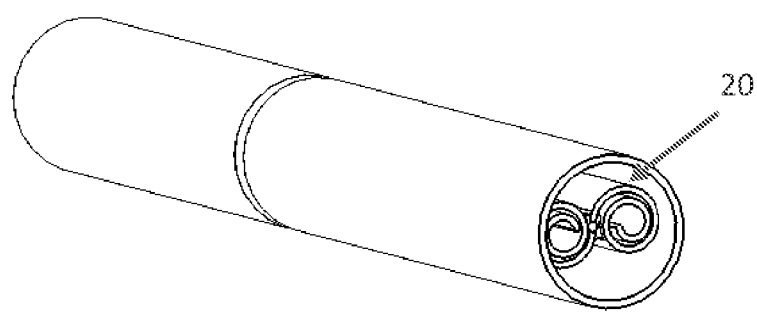
FIG. 4 is a schematic illustration of the bladder of FIGS. 1A-G rolled and inserted into a delivery sheath.

First and second bladder-mounting pins 40 are removed from the first and the second rolled portions of bladder 20, and bladder 20 is inserted into a delivery sheath 130, such as shown in FIG. 4, described hereinbelow. The pins may be removed before or after insertion of the bladder into the delivery sheath.

Alternatively, for some applications, a single bladder-mounting pin 40 is used for rolling both first and second portions 62A and 62B of bladder 20. After rolling first portion 62A, bladder-mounting pin 40 is removed from first rolled portion 62A of bladder 20 (either while bladder-mounting pin 40 is mounted on rolling machine 10, or after temporarily dismounting bladder-mounting pin 40 from rolling machine 10), and second portion 62B is rolled around bladder-mounting pin 40.

Figure 3A:
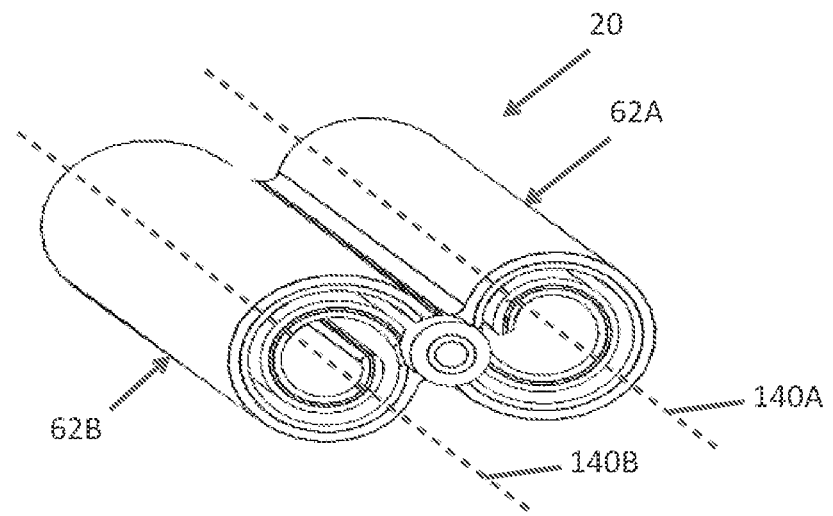
FIG. 3A is a schematic illustration of a first rolling arrangement of the bladder of FIG. 1.
Figure 3B:
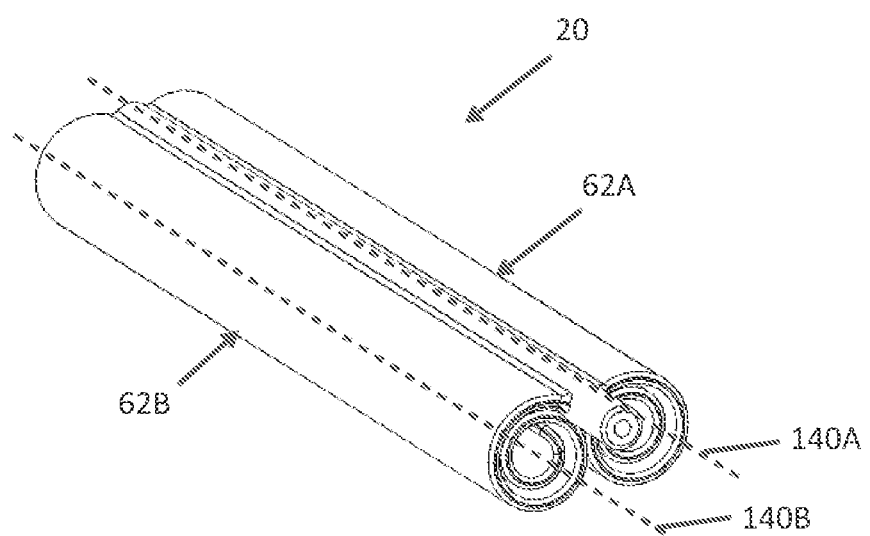
FIG. 3B is a schematic illustration of a second rolling arrangement of the bladder of FIG. 1.

Reference is made to FIGS. 3A and 3B, which are schematic illustrations of two rolling arrangements of bladder 20. As a result of the two-phase rolling process described hereinabove, bladder 20 is rolled about two different axes (defined by first and second bladder-mounting pins 40 before they are removed), rather than about a single central axis. Such two-axis rolling facilitates easy unrolling of the two portions (e.g., halves) of bladder 20 in small and narrow spaces, e.g., spaces in human joints, such as between a ball and socket.

For some applications, such as shown in FIG. 3A, first portion 62A and second portion 62B are rolled in the same direction around their respective central axes 140A and 140B, such that bladder 20 is rolled in an overly curled S-shape. For some applications, in order to produce this rolling arrangement, rolling pin 32 is rotated to roll first portion 62A in a rotational direction around first bladder-mounting pin 40, the partially-rolled bladder 20 is turned over (such that the remaining unrolled surface that faced downward now faces upward), second portion 62B is inserted between rolling pin 32 and second bladder-mounting pin 40, and rolling pin 32 is rotated to roll second portion 62B in the same rotational direction around second bladder-mounting pin 40. The direction may be either clockwise or counterclockwise. For some applications, to turn over partially-rolled bladder 20, the bladder is rotated about an axis of delivery rod 120.

For some applications, such as shown in FIG. 3B, first portion 62A and second portion 62B are rolled in opposite directions around their respective central axes 140A and 140B, such that bladder 20 is rolled in a cassette-tape-like configuration.

For some applications, in order to produce the rolling arrangement shown in FIG. 3B, rolling pin 32 is rotated to roll first portion 62A in a rotational direction around first bladder-mounting pin 40, second portion 62B is inserted between rolling pin 32 and second bladder-mounting pin 40 (without turning over the partially-rolled bladder 20), and rolling pin 32 is rotated to roll second portion 62B in the same rotational direction around second bladder-mounting pin 40. The direction may be either clockwise or counterclockwise. For some of these applications, in order to insert second portion 62B between the pins, delivery rod 120 is reoriented to extend 180 degrees in the opposite direction from its initial direction during rolling of first portion 62A (e.g., in FIG. 1C, delivery rod 120 extends down and to the right of bladder 20 during rolling of first portion 62A, and up and to the left of bladder during rolling of second portion 62B); feeding unit 80 may optionally be reoriented together with delivery rod 120 (and handle 122).

For other applications, in order to produce the rolling arrangement shown in FIG. 3B:
- rolling pin 32 is rotated to roll first portion 62A in a first rotational direction around first bladder-mounting pin 40 (either clockwise or counterclockwise),
- second bladder-mounting pin 40 is mounted to support structure 30 on an opposite vertical side of rolling pin 32 from the vertical side during rolling of first portion 62A (e.g., below rolling pin 32 if mounted above rolling pin 32 during rolling of first portion 62A, such as shown in the figures),
- the partially-rolled bladder 20 is turned over (such that the remaining unrolled surface that faced downward now faces upward) (for some applications, to turn over partially-rolled bladder 20, the bladder is rotated about an axis of delivery rod 120), and
- second portion 62B is inserted between rolling pin 32 and second bladder-mounting pin 40, and rolling pin 32 is rotated to roll second portion 62B around second bladder-mounting pin 40 in a second rotational direction, opposite the first rotational direction.

For applications in which rolling initiator 50 is used, the rolling initiator is typically turned over before being used to initiate the rolling of second portion 62B.

Reference is made to FIG. 4, which is a schematic illustration of bladder 20 rolled and inserted into delivery sheath 130. For example, delivery sheath 130 may have a circular, elliptical, or oval cross section.

Figure 5:
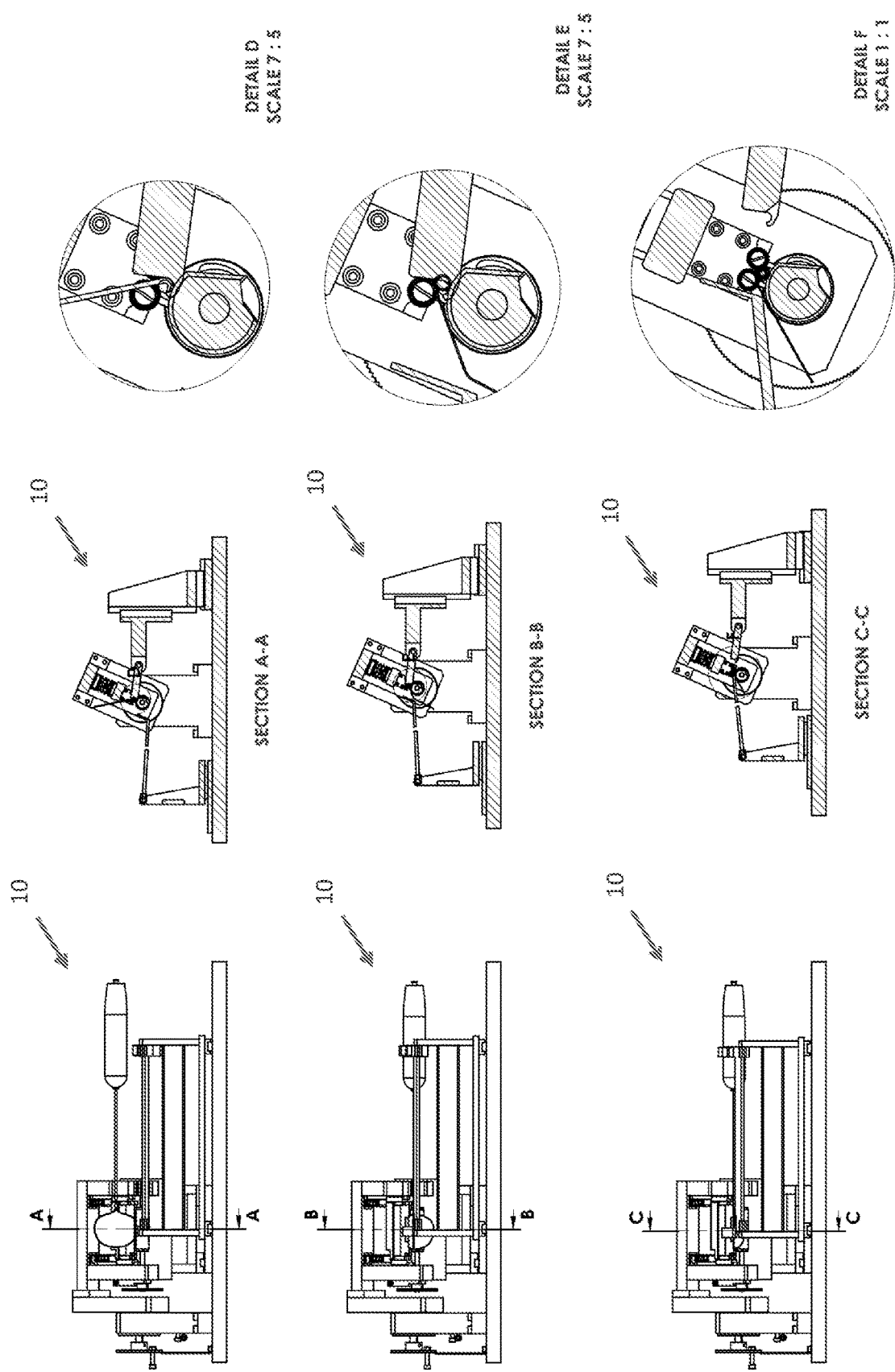
FIG. 5 includes additional illustrations of the bladder rolling machine of FIGS. 1A-G.

Reference is made to FIG. 5, which includes additional illustrations of bladder rolling machine 10.

Although bladder rolling machine 10 has been generally described herein as useful for folding joint spacer bladders, bladder rolling machine 10 may also be used for rolling other medical bladders and balloons, such for implantation in other sites in the human body, e.g., the prostate, the stomach, or for separation between soft tissues. Bladder rolling machine 10 may also be used for non-medical bladders and balloons, such as in toys.

In some implementations, techniques and apparatus described in one or more of the following applications are combined with techniques and apparatus described herein:
U.S. Pat. No. 8,221,442 to Domb et al.
U.S. Pat. No. 8,480,647 to Shohat et al.
U.S. Pat. No. 8,753,390 to Shohat
U.S. Pat. No. 8,894,713 to Shohat et al.
US 2008/0033471 to Paz et al.
US 2010/0137999 to Shohat
US 2012/0330340 to Shohat
PCT Publication WO 2008/111073 to Shohat
PCT Publication WO 2010/097724 to Shohat
PCT Publication WO 2012/017438 to Shohat et al.
PCT Publication WO 2013/057566 to Shohat It will be appreciated by persons skilled in the art that the present implementations are not limited to what has been particularly shown and described hereinabove. Rather, implementations include both combinations and subcombinations of the various features described hereinabove, as well as variations and modifications thereof that are not in the prior art, which would occur to persons skilled in the art upon reading the foregoing description.

The invention claimed is:

1. A method for rolling an inflatable bladder, the bladder including a volume between a top layer and an opposite bottom layer, the bladder capable of assuming a collapsed state and an inflated state, the bladder in the collapsed state including an edge between the top and bottom layers, the method comprising:

rolling a first portion of the bladder in the collapsed state along a first part of the edge to form a first roll defining a first axis, the top layer defining an outermost surface of the first roll, and rolling a second portion of the bladder in the collapsed state along a second part of the edge to form a second roll defining a second axis, the bottom layer defining an outermost surface of the second roll, wherein the first axis is non-coaxial with the second axis, wherein the step of rolling the first portion of the bladder in the collapsed state includes the step of rotating a first pin in a first direction such that the bottom layer contacts the first pin, and the step of rolling the second portion of the bladder in the collapsed state includes the step of rotating a second pin in the first direction such that the top layer contacts the second pin, wherein the step of rolling the first portion of the bladder in the collapsed state includes positioning the first part of the edge between the first pin and a rolling pin of a rolling machine, wherein the first pin is rotatable about the first axis, and the rolling pin is rotatable about a third axis that is non-coaxial with and parallel to the first axis.

2. The method of claim 1, wherein a distance between the first axis and the second axis is substantially the same as the sum of radii of the first and second rolls.

3. The method of claim 2, wherein the step of rolling the second portion of the bladder in the collapsed state includes positioning the second part of the edge between the second pin and the rolling pin of the rolling machine, wherein the second pin is rotatable about the second axis, and the rolling pin is rotatable about a fourth axis that is non-coaxial with and parallel to the second axis.

4. The method of claim 3, further comprising a step of dismounting the first pin and installing the second pin to the rolling machine after performing the step of rolling the first roll.

5. The method of claim 3, wherein the step of rolling the first portion of the bladder in the collapsed state includes the step of using a rolling initiator mounted on the rolling machine to position and roll the first part of the edge between the first pin and the rolling pin of the rolling machine, and the step of rolling the second portion of the bladder in the collapsed state includes the step of using the rolling initiator to position and roll the second part of the edge between the second pin and the rolling pin of the rolling machine.

6. The method of claim 3, further comprising a step of using a clamp to hold the first and second rolls during rolling around the first and second pins respectively.

7. The method of claim 3, further comprising a step of removing the first pin from the first roll and a step of removing the second pin from the second roll and placing the first and second rolls into a delivery sheath.

8. A method for rolling an inflatable bladder, the bladder including a volume between a top layer and an opposite bottom layer, the bladder capable of assuming a collapsed state and an inflated state, the bladder in the collapsed state including an edge between the top and bottom layers, the method comprising:

rolling a first portion of the bladder in the collapsed state along a first part of the edge to form a first rolled section defining a first axis, the top layer defining an outer surface of the first rolled section, and rolling a second portion of the bladder in the collapsed state along a second part of the edge to form a second rolled section defining a second axis, the top layer defining an outer surface of the second rolled section, wherein the first axis is non-coaxial with the second axis, wherein the step of rolling the first portion of the bladder in the collapsed state includes positioning the first part of the edge between a first pin and a rolling pin of a rolling machine, wherein the first pin is rotatable about the first axis, and the rolling pin is rotatable about a third axis that is non-coaxial with and parallel to the first axis.

9. The method of claim 8, wherein a distance between the first axis and the second axis is substantially the same as the sum of radii of the first and second rolled sections.

10. The method of claim 8, wherein the step of rolling the first portion of the bladder in the collapsed state includes the step of rotating the first pin in a first direction such that the bottom layer contacts the first pin, and the step of rolling the second portion of the bladder in the collapsed state includes the step of rotating a second pin in a second direction opposite the first direction such that the bottom layer contacts the second pin.

11. The method of claim 10, wherein the step of rolling the second portion of the bladder in the collapsed state includes positioning the second part of the edge between the second pin and the rolling pin of the rolling machine, wherein the second pin is rotatable about the second axis, and the rolling pin is rotatable about a fourth axis that is non-coaxial with and parallel to the second axis.

12. The method of claim 11, further comprising a step of dismounting the first pin and installing the second pin to the rolling machine after performing the step of rolling the first rolled section.

13. The method of claim 11, wherein the step of rolling the first portion of the bladder in the collapsed state includes the step of using a rolling initiator mounted on the rolling machine to position and roll the first part of the edge between the first pin and the rolling pin of the rolling machine, and the step of rolling the second portion of the bladder in the collapsed state includes the step of using the rolling initiator to position and roll the second part of the edge between the second pin and the rolling pin of the rolling machine.

14. The method of claim 11, further comprising a step of using a clamp to hold the first and second rolled sections during rolling around the first and second pins respectively.

15. The method of claim 11, further comprising a step of removing the first pin from the first rolled section and a step of removing the second pin from the second rolled section and placing the first and second rolled sections into a delivery sheath.

16. A method for rolling an inflatable bladder, the bladder including a volume between a top layer and an opposite bottom layer, the bladder capable of assuming a collapsed state and an inflated state, the bladder in the collapsed state including an edge between the top and bottom layers, the method comprising: rolling a first portion of the bladder around a first axis by rotating a pin in a first direction such that the top layer contacts the pin to form a first roll, the top layer defining an outermost surface of the first roll, and rolling a second portion of the bladder around a second axis by rotating the pin in the first direction such that the bottom layer contacts the pin to form a second roll, the bottom layer defining an outermost surface of the second roll, wherein the first axis is non-coaxial with the second axis, wherein the step of rolling the first portion of the bladder in the collapsed state includes positioning the first part of the edge between the pin and a rolling pin of a rolling machine, wherein the pin is rotatable about the first axis, and the rolling pin is rotatable about a third axis that is non-coaxial with and parallel to the first axis.

* * * * *